United States Patent
Narimatsu (10) Patent No.: US 6,746,405 B2
(45) Date of Patent: Jun. 8, 2004

(54) BLOOD PRESSURE MEASURING APPARATUS WITH PULSE WAVE DETECTING FUNCTION

(75) Inventor: Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/397,201

(22) Filed: Mar. 27, 2003

(65) Prior Publication Data

US 2004/0059232 A1 Mar. 25, 2004

(30) Foreign Application Priority Data

Sep. 19, 2002 (JP) ........................................ 2002-273911

(51) Int. Cl.$^7$ ................................................. A61B 5/00
(52) U.S. Cl. ........................ 600/494; 600/490; 600/495
(58) Field of Search .................................. 600/485, 490, 600/493–6

(56) References Cited

U.S. PATENT DOCUMENTS 5,170,795 A * 12/1992 Ramsey et al. ............. 600/495
5,931,790 A * 8/1999 Peel, III ..................... 600/494
6,582,374 B2 * 6/2003 Yokozeki .................... 600/494

FOREIGN PATENT DOCUMENTS

| JP | A 2001-190509 | | 7/2001 | |
| JP | 2002136487 | * | 5/2002 | ................. 600/490 |

OTHER PUBLICATIONS

Toshio Ozawa et al., "Pulse–Wave Velocity," *Medical View*, 1$^{st}$ Edition, pp. 18–25 (2002).

* cited by examiner

*Primary Examiner*—Robert L. Nasser
(74) *Attorney, Agent, or Firm*—Oliff & Berridge, PLC (57) ABSTRACT

A blood pressure measuring apparatus, including a cuff adapted to be worn on a body portion of a living subject, and determining a blood pressure value of the subject based on a signal obtained from the cuff when a pressure in the cuff is changed, wherein the apparatus includes: a cuff pulse wave detecting device which detects a cuff pulse wave as a pulse wave produced from an artery of the subject and transmitted to the cuff, the cuff pulse wave comprising at least one heartbeat-synchronous pulse produced from the artery in synchronism with at least one heartbeat of the subject; a converting device which converts, based on the blood pressure value determined by the apparatus, a magnitude of each point of the heartbeat-synchronous pulse of the cuff pulse wave, into a pressure value; and a pseudo-pressure-pulse-wave determining device which determines a pseudo pressure pulse wave by correcting the respective pressure values of the respective points of the pulse, provided by the converting device, according to at least one correction relationship between (A) proportion of difference of pressure value of each point of heartbeat-synchronous pulse from pressure value of minimum point of the pulse, to pulse pressure as difference of pressure value of maximum point of the pulse from the pressure value of the minimum point of the pulse, and (B) correction amount, in which greater correction amount corresponds to greater proportion.

7 Claims, 8 Drawing Sheets

BLOOD PRESSURE MEASURING APPARATUS WITH PULSE WAVE DETECTING FUNCTION

BACKGROUND OF THE INVENTION

1. Field of the Invention

The present invention relates to a blood pressure measuring apparatus having a function of detecting a pulse wave to be analyzed.

2. Related Art Statement

A pulse wave produced from an artery of a living subject, i.e., an arterial pulse wave provides a plurality of sorts of information on the physical condition of the subject. In view of this, the pulse wave is often analyzed for diagnosing the physical condition of the subject. For instance, an augmentation index (AI) is determined or obtained based on the arterial pulse wave, for evaluating arteriosclerosis.

As described in "Pulse-Wave Velocity" pages 18, 19, 22, 1st edition, May 1, 2002, by Toshio OZAWA and Yoshiaki MASUDA, published by MEDICAL VIEW, the augmentation index is calculated as a proportion of a difference between a height (magnitude) of a tidal wave, and a height (magnitude) of a percussion wave, of a heartbeat-synchronous pulse of the arterial pulse wave, to a height (magnitude) of a maximum point of the heartbeat-synchronous pulse of the arterial pulse wave. Since, as arteriosclerosis advances, a reflected-wave component of the pulse wave returns back faster than normal, the magnitude of the tidal wave becomes greater than that of the percussion wave, and the augmentation index increases.

The arterial pulse wave may be invasively obtained by inserting a pressure-sensing element or a catheter directly in the artery of the subject. Clinically, there is used a pressure pulse wave which is obtained by using a pulse wave detector, because this method is easier for obtaining the pulse wave than the invasive method. As the pulse wave detector, there is often used a multi-sensor-type pulse wave detector (available from Colin Corporation, Japan) as described in the above-indicated document. The multi-sensor-type pulse wave detector has about thirty sensors, and is arranged to record automatically the optimum one of respective waveforms detected by the thirty sensors, the optimum waveform having the greatest SIN ratio. The thus arranged multi-sensor-type pulse wave detector is convenient for detecting the pulse wave since the detector can be used without skill. The multi-sensor-type pulse wave detector is disclosed in JP-A-2001-190509, for instance. The disclosed multi-sensor-type pulse wave detector employs a so-called "tonometric method" wherein a pressure pulse wave sensor is adapted to be pressed against an artery of a subject such that a portion of the wall of the artery is substantially flattened, for detecting a pressure pulse wave.

The above-described multi-sensor-type pulse wave detector as the tonometric-type sensor is expensive, and needs cumbersome operation for detecting the pressure pulse wave. Accordingly, there has been a need to utilize and analyze, for making a diagnosis on a patient, a cuff pulse wave obtained from a cuff by using a cuff-equipped blood pressure measuring apparatus which is widely used since it is inexpensive and simple to handle. However, as the cuff pulse wave is a volumetric pulse wave representing a volume of blood, the waveform of the cuff pulse wave is not completely identical with that of the pressure pulse wave detected through the above-described pulse wave detector. Accordingly, the knowledge which has conventionally been obtained by analyzing the pressure pulse wave detected through the pulse wave detector cannot be readily utilized in diagnosing a patient based on a cuff pulse wave.

SUMMARY OF THE INVENTION

It is therefore an object of the present invention to provide a blood pressure measuring apparatus with a pulse-wave detecting function, the apparatus being capable of converting a waveform of a cuff pulse wave into a waveform of a pressure pulse wave.

As a result of an extensive study made by the inventor, it has been found that the difference between the waveform of the cuff pulse wave and the waveform of the pressure pulse wave increases in a direction toward the maximum or peak point of the cuff pulse wave, and that the amount of difference between the waveform of the cuff pulse wave and the waveform of the pressure pulse wave depends on a proportion of a difference of a height or magnitude of each point of the waveform of the cuff pulse wave from a height or magnitude of a minimum point of the waveform, to a pulse pressure as the difference of a magnitude of a maximum point from the magnitude of the minimum point of the pulse. The present invention has been developed based on these findings.

The above-indicated object of the present invention has been achieved by the present invention. According to the present invention, there is provided a blood pressure measuring apparatus, comprising a cuff which is adapted to be worn on a body portion of a living subject, and determining a blood pressure value of the subject based on a signal which is obtained from the cuff when a pressure in the cuff is changed, wherein the apparatus further comprises: a cuff pulse wave detecting device which detects a cuff pulse wave as a pulse wave which is produced from an artery of the subject and is transmitted to the cuff, the cuff pulse wave comprising at least one heartbeat-synchronous pulse which is produced from the artery in synchronism with at least one heartbeat of the subject; a converting means for converting, based on the blood pressure value determined by the apparatus, a magnitude of each point of the heartbeat-synchronous pulse of the cuff pulse wave, into a pressure value; and a pseudo-pressure-pulse-wave determining means for determining a pseudo pressure pulse wave by correcting the respective pressure values of the respective points of the heartbeat-synchronous pulse, provided by the converting means, according to at least one correction relationship between (A) proportion of difference of pressure value of each point of heartbeat-synchronous pulse from pressure value of minimum point of the pulse, to pulse pressure as difference of pressure value of maximum point of the pulse from the pressure value of the minimum point of the pulse, and (B) correction amount, in which greater correction amount corresponds to greater proportion.

In the present blood pressure measuring apparatus, the converting means converts, based on the blood pressure value determined by the blood pressure measuring apparatus, a magnitude of each point of the heartbeat-synchronous pulse of the cuff pulse wave detected by the cuff pulse wave detecting device, into a pressure value. Subsequently, the pseudo-pressure-pulse-wave determining means determines the pseudo pressure pulse wave by correcting the respective pressure values of the respective points of the heartbeat-synchronous pulse. Therefore, the determined pseudo pressure pulse wave can be effectively utilized for making a diagnosis on the patient, without a need of detecting a pressure pulse wave by using the pressure pulse wave detector that is expensive and difficult or cumbersome to handle.

It is noted that, in a first portion of the pulse of the cuff pulse wave that precedes the maximum point of the pulse, the amount of difference between the waveform of the cuff pulse wave and the waveform of the pressure pulse wave slightly differs from that in a second portion of the pulse of the cuff pulse wave that follows the maximum point of the pulse. In view of this, preferably, the pseudo-pressure-pulse-wave determining means determines a first portion of the pseudo pressure pulse wave by correcting the respective pressure values of the respective points of the first portion of the heartbeat-synchronous pulse that precedes the maximum point of the pulse, according to a first correction relationship, and determines a second portion of the pseudo pressure pulse wave by correcting the respective pressure values of the respective points of the second portion of the pulse that follows the maximum point of the pulse, according to a second correction relationship differing from the first correction relationship. According to this arrangement, the pseudo pressure pulse wave determined by the pseudo-pressure-pulse-wave determining means becomes more similar to a true pressure pulse wave, so that a more accurate diagnosis can be made by using the determined pseudo pressure pulse wave.

Preferably, the pseudo-pressure-pulse-wave determining means selects, from a plurality of correction relationships corresponding to a plurality of pulse-pressure ranges, one correction relationship based on a pulse pressure determined based on the blood pressure value determined by the apparatus, and determines the pseudo pressure pulse wave by correcting the respective pressure values of the respective points of the heartbeat-synchronous pulse, according to said one correction relationship. According to this arrangement, the correction relationship used where the pulse pressure is small differs from that used where the pulse pressure is great, so that the determined pseudo pressure pulse wave becomes more similar to a true pressure pulse wave.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
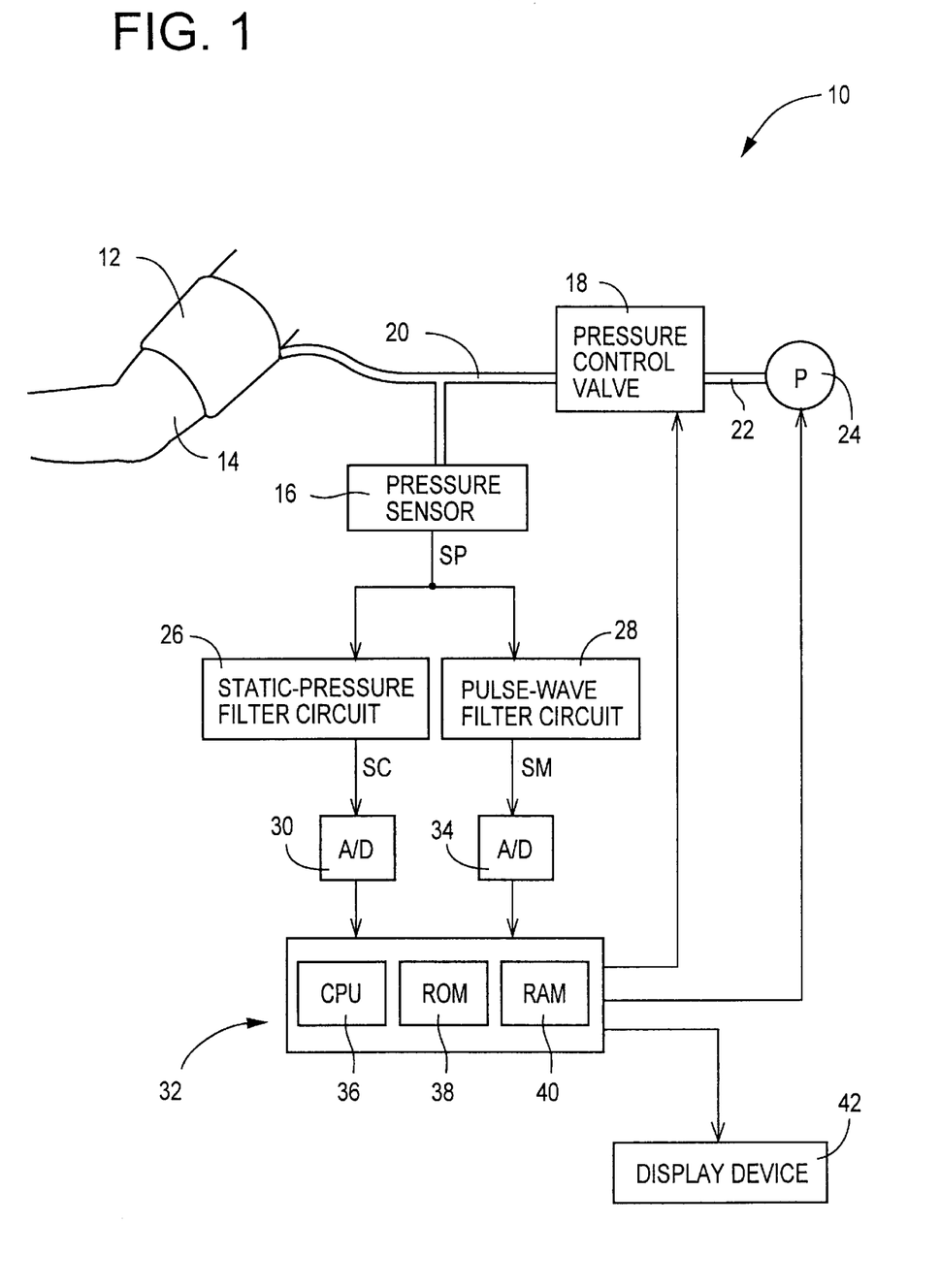
FIG. 1 is a view for explaining a construction of a blood pressure measuring apparatus with a pulse-wave detecting function, according to the present invention.

Hereinafter, there will be described one embodiment of the present invention, by reference to the drawings. FIG. 1 is a diagrammatic view for explaining the construction of a blood pressure (BP) measuring apparatus 10 to which the present invention is applied.

As shown in FIG. 1, the present BP measuring apparatus 10 includes a cuff 12 which has a belt-like cloth bag and a rubber bag accommodated in the cloth bag and which is adapted to be wound around an upper arm 14 of a patient as a living subject, a pressure sensor 16 and a pressure control valve 18. The pressure sensor 16 and the pressure control valve 18 are connected to the cuff 12 via a pipe 20. An air pump 24 is connected to the pressure control valve 18 via a pipe 22. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal SP representing the detected air pressure, to a static-pressure filter circuit 26 and a pulse-wave filter circuit 28. The static-pressure filter circuit 26 has a low-pass filter and extracts, from the pressure signal SP, a cuff-pressure signal SC representing a static-pressure component contained in the signal SP, i.e., a pressing pressure of the cuff 12 (hereinafter referred to as "cuff pressure PC"). The cuff-pressure signal SC is supplied to an electronic control device 32 which will be described, via an analog-to-digital (A/D) converter 30. The pulse-wave filter circuit 28 includes a band-pass filter which transmits a frequency component of the pressure signal SP that has frequencies in a range of about 1 to 30 Hz, and extracts, from the pressure signal SP, a cuff-pulse-wave signal SM. The cuff-pulse-wave signal SM is supplied to the control device 32 via an A/D converter 34. The cuff-pulse-wave signal SM represents a cuff pulse wave which is produced from a brachial artery (not shown) of the upper arm 14 of the subject and is transmitted to the cuff 12. Accordingly, the pressure sensor 16 and the pulse-wave filter circuit 28 cooperate with each other to provide a cuff pulse wave detecting device which detects the cuff pulse wave from the cuff 12. The cuff pulse wave includes at least one heartbeat-synchronous pulse which is produced from the artery in synchronism with at least one heartbeat of the subject.

The electronic control device 32 is essentially provided by a so-called microcomputer including a CPU (central processing unit) 36, a ROM (read only memory) 38, a RAM (random access memory) 40, an input-and-output (I/O) port, not shown, etc, and the CPU 36 processes signals according to control programs pre-stored in the ROM 38, while utilizing a temporary-storage function of the RAM 40. The control device 32 outputs, from the I/O port, drive signals to the air pump 24 and the pressure control valve 18 so as to control the respective operations thereof and thereby control the cuff pressure PC. In addition, the CPU 36 determines, according to the control functions shown in FIG. 2, which will be described in greater detail, a pseudo pressure pulse wave based on the cuff pulse wave, and further determines an augmentation index (AI) based on the determined pseudo pressure pulse wave. In addition, the CPU 36 controls a display device 42 to display the determined pseudo pressure pulse wave and augmentation index AI.

Figure 2:
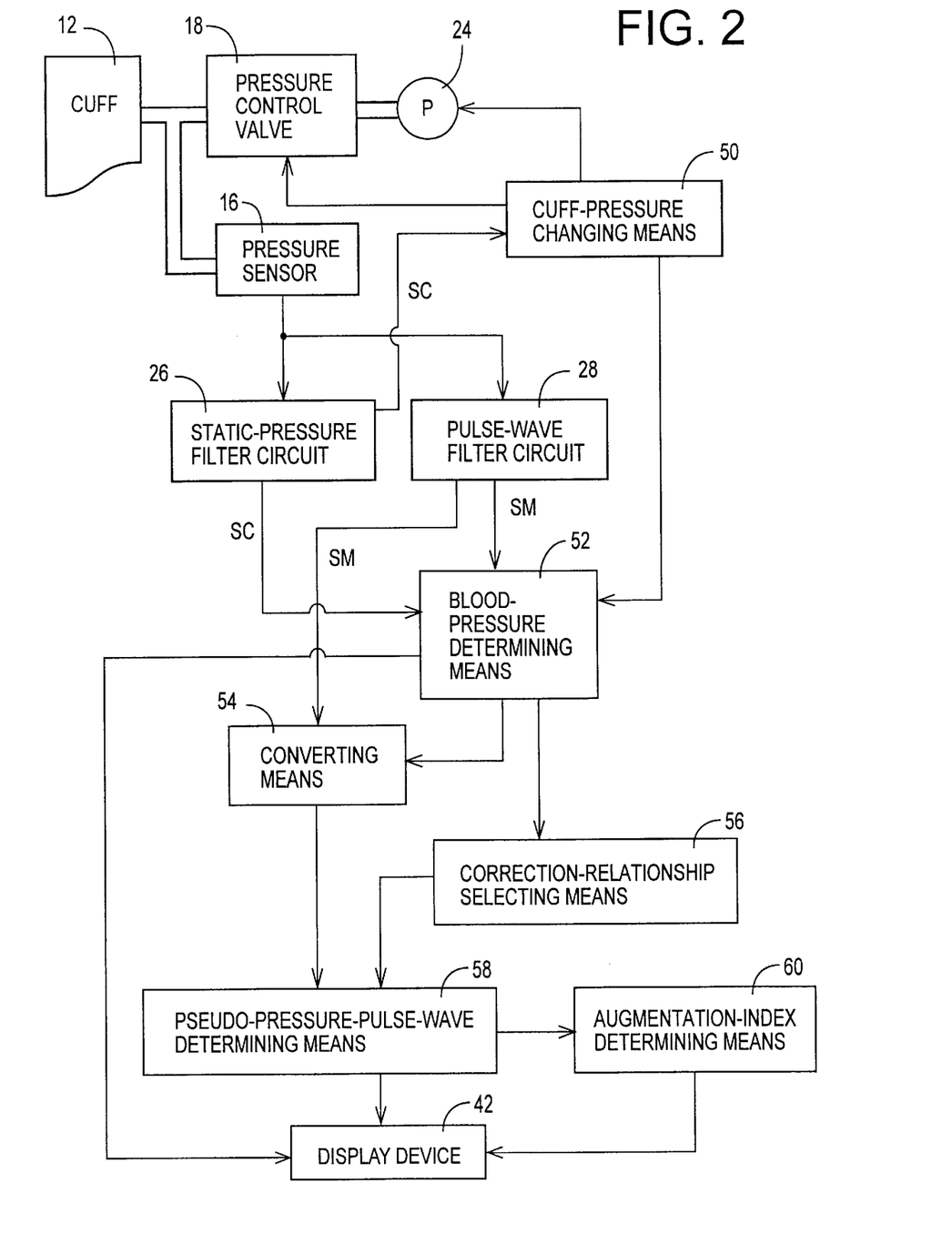
FIG. 2 is a diagrammatic view for explaining essential control functions of a CPU (central processing unit) of a control device of the apparatus of FIG. 1.

FIG. 2 is a block diagram for explaining essential control functions of the CPU 36 of the present BP measuring apparatus 10.

A cuff-pressure changing means or device 50 operates the pressure control valve 18 and the air pump 24 so as to keep, for a time period corresponding to a not less than one heartbeat length, the cuff pressure PC at a pre-set pulse-wave detecting pressure PC1, thereafter, quickly increase the cuff pressure PC to a pre-set target pressure PC2 (e.g., 180 mmHg) that would be higher than a systolic blood pressure $BP_{SYS}$ of the upper arm 14 of the subject and, subsequently, slowly decrease the cuff pressure PC at a pre-set rate of, e.g., 2 or 3 mmHg/sec until a blood-pressure determining means or device 52, described below, determines a blood pressure BP of the subject. After the blood pressure BP of the subject has been determined by the blood-pressure determining means 52, the cuff pressure PC is released to an atmospheric pressure.

The above-described pulse-wave detecting pressure PC1 is pre-set to be lower than a mean blood pressure $BP_{MEAN}$ of the subject, preferably lower than a diastolic blood pressure $BP_{DIA}$, but permit the cuff pulse wave to have a sufficiently great magnitude. The pulse-wave detecting pressure PC1 is pre-set at 50 mmHg or 60 mmHg, for instance. The reason for pre-setting the pulse-wave detecting pressure PC1 to the above-described level is as follows. If the cuff pressure PC is higher than the diastolic blood pressure $BP_{DIA}$, the waveform of the cuff-pressure signal SM extracted by the pulse-wave filter circuit 28 and indicative of the cuff pulse wave is deformed due to compression of the blood vessel. Especially when the cuff pressure PC is higher than the mean blood pressure $BP_{MEAN}$, the waveform of the cuff-pulse wave signal SM is deformed to a greater extent due to a greater degree of compression of the blood vessel. On the other hand, if the cuff pressure PC is too low, the cuff pulse wave does not have a sufficiently great magnitude.

The blood-pressure determining means 52 determines, according to a well-known oscillometric method, a systolic blood pressure value $BP_{SYS}$, a mean blood pressure value $BP_{MEAN}$, and a diastolic blood pressure value $BP_{DIA}$ of the upper arm 14 of the subject, based on the variation of respective amplitudes of pulses of the cuff pulse wave represented by the cuff-pulse-wave signal SM continuously supplied from the pulse-wave filter circuit 28, and the cuff-pressure signal SC continuously supplied from the static-pressure filter circuit 26, during the slow decreasing of the cuff pressure PC under the control of the cuff-pressure changing means 50. The thus determined blood pressure values $BP_{SYS}$, $BP_{MEAN}$, $BP_{DIA}$ are displayed by the display device 42. The display device 42 may be either an optical display or a printer using ink.

Figure 3:
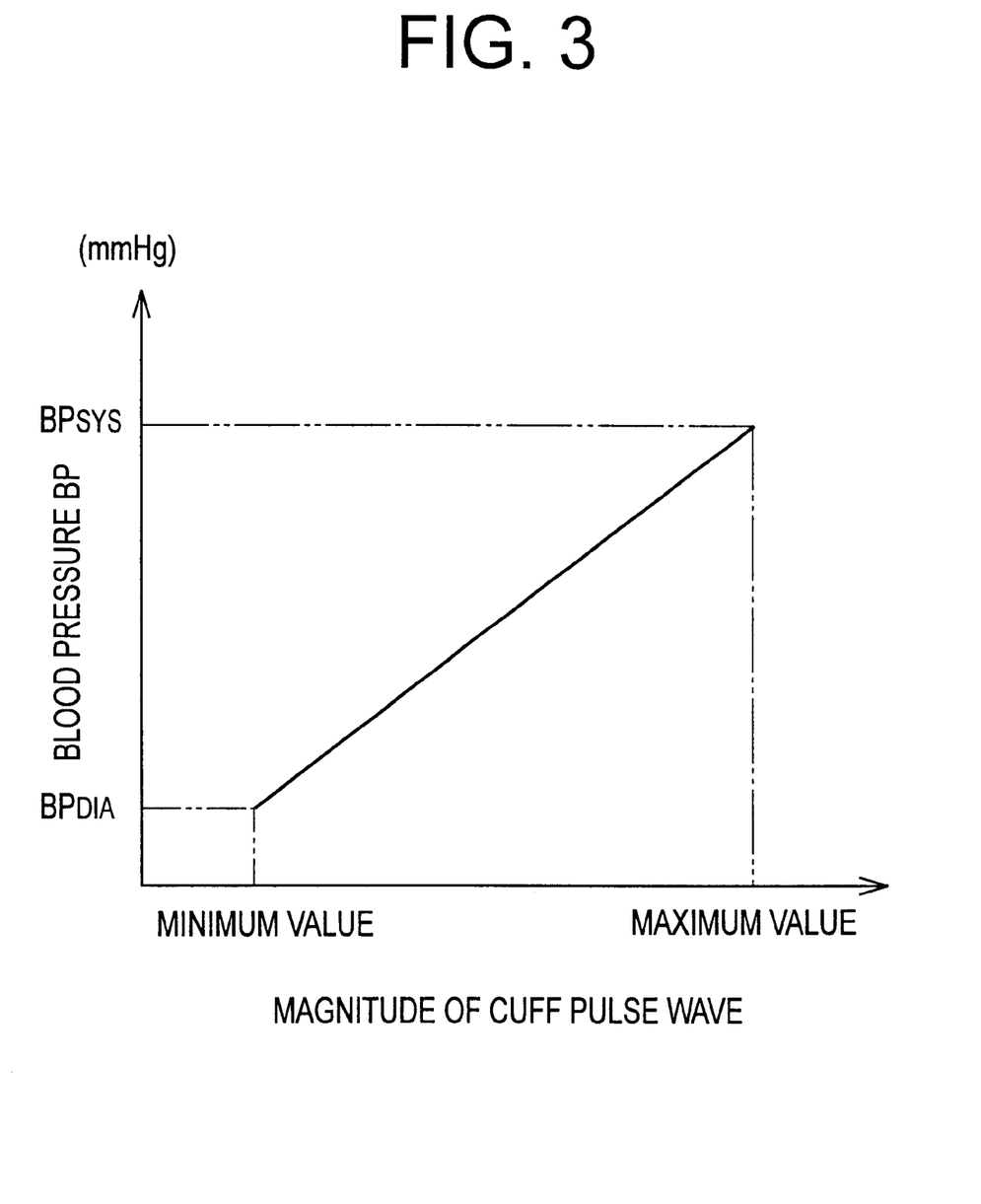
FIG. 3 is a view showing a relationship used to convert a magnitude of a cuff pulse wave into a blood pressure BP.

A converting means or device 54 converts a magnitude of each point of the cuff-pulse-wave signal SM (the cuff pulse wave) extracted by the pulse-wave filter circuit 28 with the cuff pressure PC being kept at the pulse-wave detecting pressure PC1 by the cuff-pressure changing means 50, into a pressure value, based on the diastolic blood pressure $BP_{DIA}$ and the systolic blood pressure $BP_{SYS}$ determined by the blood-pressure determining means 52. Described more specifically, the converting means 54 converts the magnitude of each point of the pulse of the cuff pulse wave into the pressure value, according to a relationship between magnitude of cuff pulse wave and blood pressure BP, the relationship being represented by a straight line shown in FIG. 3. In the relationship shown in FIG. 3, a minimum magnitude of a pulse of a cuff pulse wave corresponds to a diastolic blood pressure $BP_{DIA}$, and a maximum magnitude of the pulse corresponds to a systolic blood pressure $BP_{SYS}$.

Figure 4A:
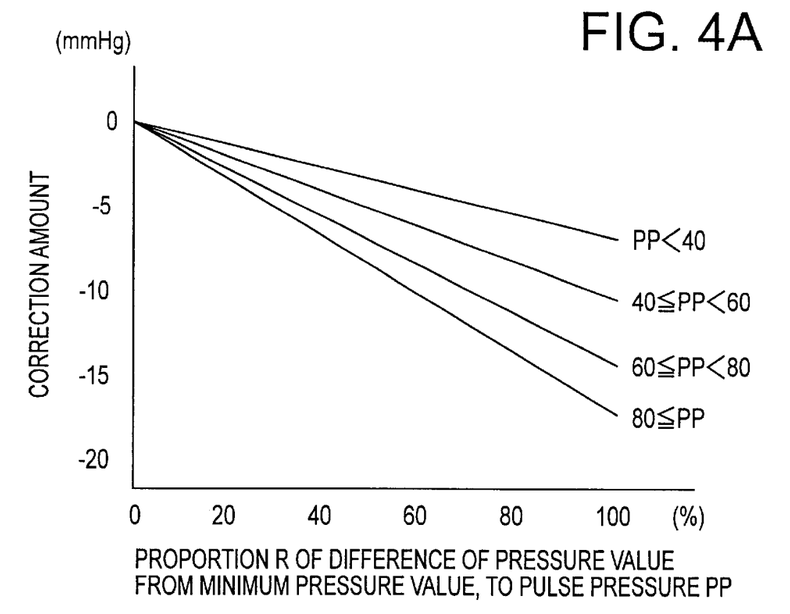
FIGS. 4A and 4B are views each showing a relationship stored in a ROM (read only memory) and used to correct the cuff pulse wave.
Figure 4B:
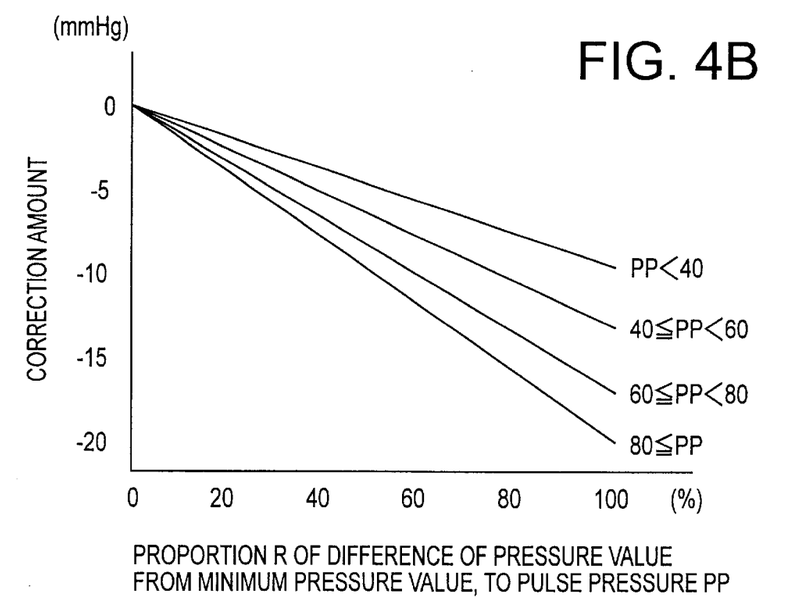

A correction-relationship selecting means or device 56 first calculates a pulse pressure PP of the pulse of the cuff pulse wave as a difference between the systolic blood pressure $BP_{SYS}$ and the diastolic blood pressure $BP_{DIA}$ which are determined by the blood-pressure determining means 52. Based on the calculated pulse pressure PP, the correction-relationship selecting means 56 selects, from a plurality of correction relationships pre-stored in the ROM 38, at least one correction relationship to be used for correcting the pressure value of each point of the pulse of the cuff pulse wave, provided by the converting means 54. FIGS. 4A and 4B show examples of the plurality of correction relationships pre-stored in the ROM 38.

FIG. 4A shows a plurality of first correction relationships used for correcting the respective pressure values of the respective points of a first portion of the pulse of the cuff pulse wave that precedes the maximum point of the pulse, and FIG. 4B shows a plurality of second correction relationships used for correcting the respective pressure values of the respective points of a second portion of the pulse of the cuff pulse wave that follows the maximum point of the pulse. In the present embodiment, four first correction relationships (FIG. 4A) and four second correction relationships (FIG. 4B) are prepared so as to correspond to four pulse-pressure ranges. Each of the first and second correction relationships is determined such that the correction amount increases with the increase of a proportion R of a difference of the pressure value of each point of the pulse of the cuff pulse wave from the pressure value of the minimum point of the pulse, to the pulse pressure PP. Where the ROM 38 pre-stores both of the first correction relationships shown in FIG. 4A used for correcting the pressure value of each point of the first portion of the pulse that precedes the maximum point of the pulse, and the second correction relationships shown in FIG. 4B used for correcting the pressure value of each point of the second portion of the pulse that follows the maximum point of the pulse, the correction-relationship selecting means 56 selects one first correction relationship and one second correction relationship. Those correction relationships are pre-determined based on cuff pulse waves, and pressure pulse waves that are obtained through a tonometric sensor, the cuff pulse waves and the pressure pulse waves being obtained from a plurality of living subjects.

Figure 5:
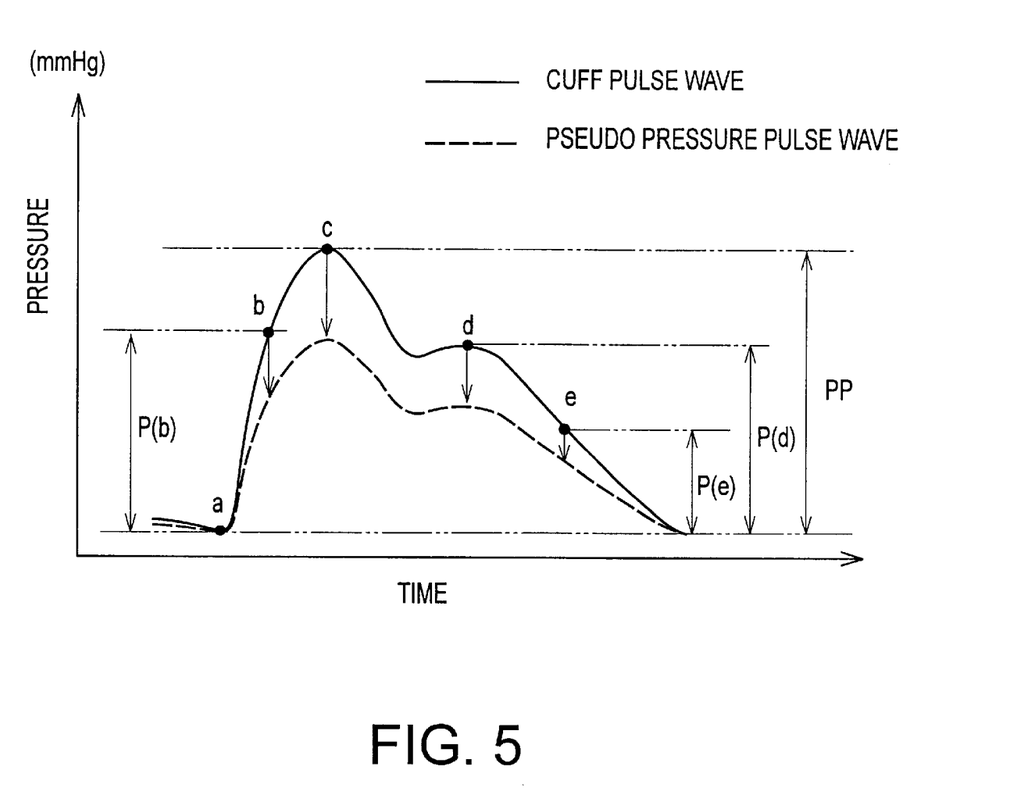
FIG. 5 is a view in which a pseudo pressure pulse wave and the cuff pulse wave whose respective points have respective pressure values are superposed on each other, the view explaining a manner in which a pseudo-pressure-pulse-wave determining means shown in FIG. 2 corrects the cuff pulse wave into the pseudo pressure pulse wave.

A pseudo-pressure-pulse-wave determining means or device 58 determines a pseudo pressure pulse wave by correcting the respective pressure values of the respective points of the pulse of the cuff pulse wave, provided by the converting means 54, according to the first and second correction relationships selected by the correction-relationship selecting means 56. FIG. 5 shows the cuff pulse wave whose respective points have been converted into the respective pressure values, on which the pseudo pressure pulse wave is superposed, the pseudo pressure pulse wave being determined by the pseudo-pressure-pulse-wave determining means 58 by correcting the pressure values of the respective points of the pulse of the cuff pulse wave. In FIG. 5, a difference of a pressure value of point "a" as the minimum point of the pulse of the cuff pulse wave from the minimum pressure value of the pulse is zero, so that a proportion R of the pressure value of the point "a" to the pulse pressure PP is 0%. Therefore, the pressure value of the point "a" need not be corrected. A difference of a pressure value of point "b" of the pulse of the cuff pulse wave from the minimum pressure value of the pulse is represented by P(b), and a proportion R of the pressure value of the point "b" to the pulse pressure PP is calculated according to the following Expression (1):

$$R=(P(b)/PP) \times 100 (\%) \qquad \text{Expression (1)}$$

The pseudo-pressure-pulse-wave determining means 58 further determines a correction amount used for correcting the pressure value of the point "b" of the pulse of the cuff pulse wave, based on the calculated proportion R, according to the first correction relationship selected by the correction-relationship selecting means 56, and corrects, i.e., subtracts the determined correction amount from the pressure value of the point "b". The pseudo-pressure-pulse-wave determining means 58 determines the pseudo pressure pulse wave indicated by a broken line in FIG. 5, by correcting the respective pressure values of the respective points of the pulse, including points "c" (maximum point), "d", and "e" shown in FIG. 5.

The pseudo-pressure-pulse-wave determining means 58 operates the display device 42 to display the thus determined pseudo pressure pulse wave.

An augmentation-index determining means or device 60 determines an augmentation index AI, based on the pseudo pressure pulse wave determined by the pseudo-pressure-pulse-wave determining means 58, and operates the display device 42 to display the determined augmentation index AI. As described above, the augmentation index AI is a proportion of a difference between a magnitude of the tidal wave, and a magnitude of the percussion wave, of the pulse, to the magnitude of the pulse, i.e., pulse pressure PP. The tidal wave corresponds to a time of occurrence of a peak point of a reflected-wave component of the pulse wave, and the percussion wave corresponds to a time of occurrence of a peak point of an incident-wave component of the pulse wave. Further, the magnitude of the pulse corresponds to the pulse pressure PP. Accordingly, the augmentation-index determining means 60 determines the respective times of occurrence of the respective peak points of the incident-wave component and the reflected-wave component of the pulse of the pseudo pressure pulse wave, calculates a difference $\Delta P$ of a magnitude of the pseudo pressure pulse wave at the time of occurrence of the peak point of the incident-wave component from a magnitude of the pseudo pressure pulse wave at the time of occurrence of the peak point of the reflected-wave component, and determines the augmentation index AI, based on the calculated difference $\Delta P$ and the pulse pressure PP of the pseudo pressure pulse wave, according to the following Expression (2):

$$AI=(\Delta P/PP) \times 100 (\%) \qquad \text{Expression (2)}$$

Figure 6:
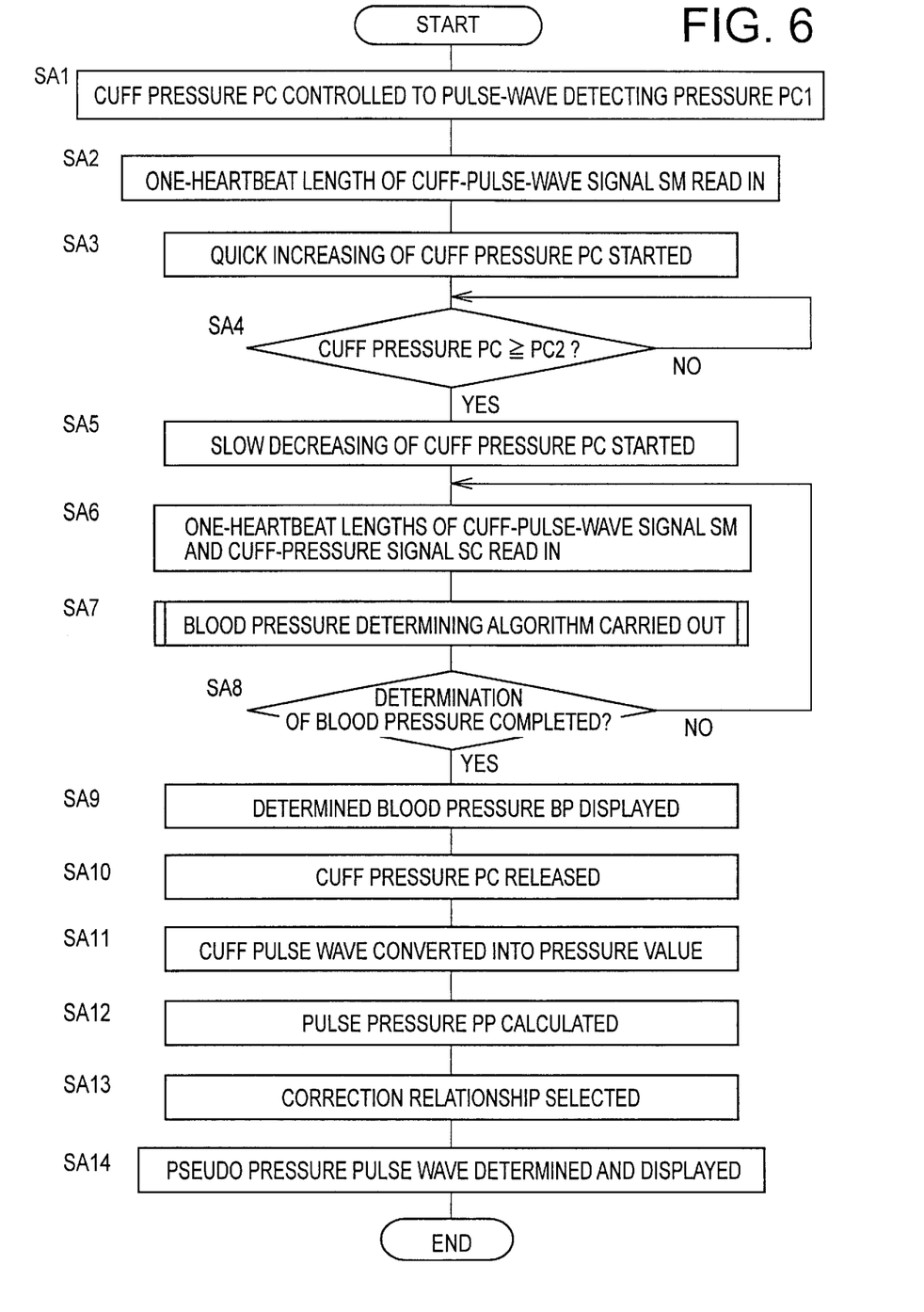
FIG. 6 is a flow chart for explaining a portion of the control functions of the CPU, shown in the diagrammatic view of FIG. 2, the flow chart representing a main routine.
Figure 7:
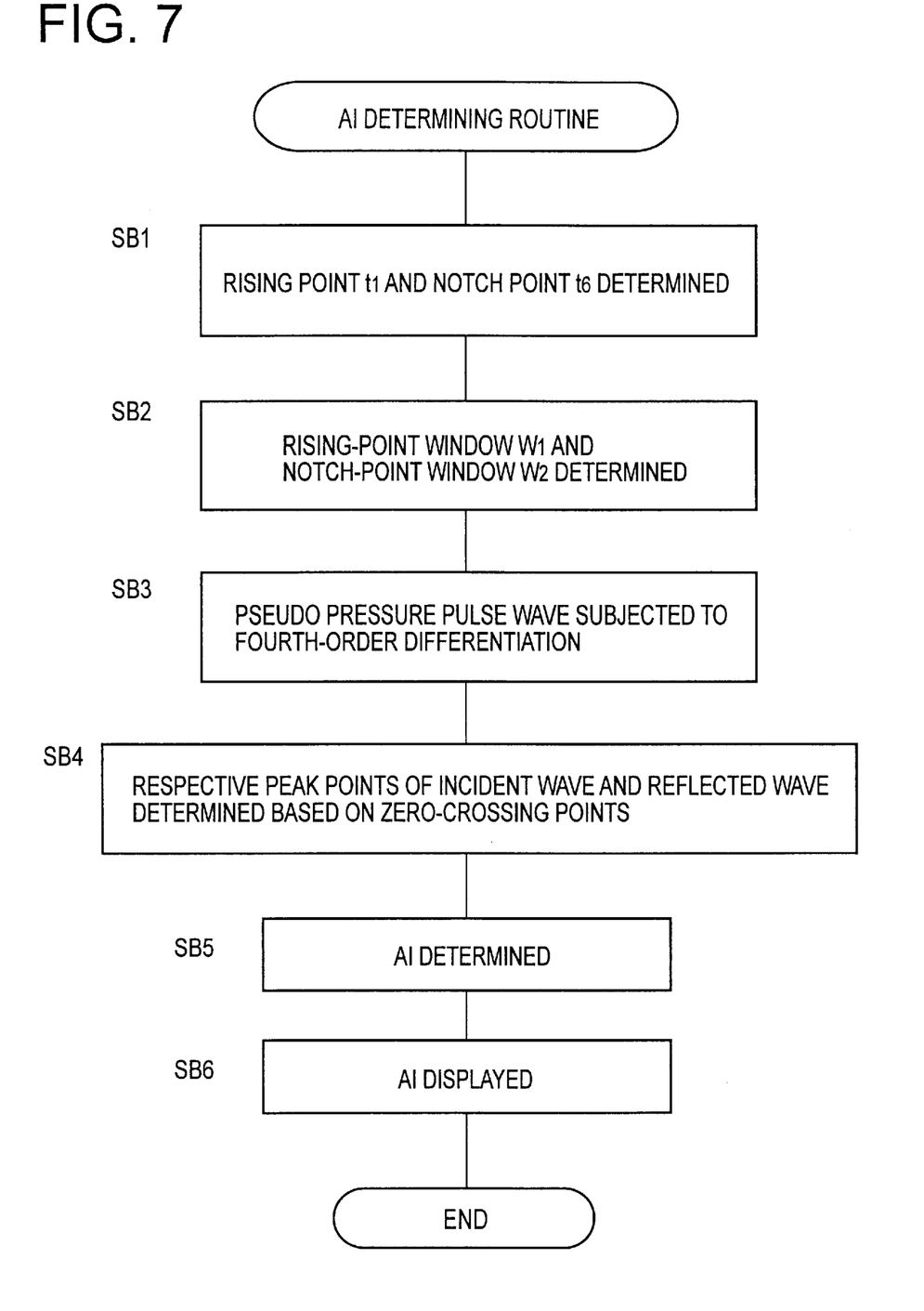
FIG. 7 is a flow chart for explaining another portion of the control functions of the CPU, shown in the diagrammatic view of FIG. 2, the flow chart representing an AI (augmentation index) determining routine.

FIGS. 6 and 7 show flow charts for explaining essential control functions of the CPU 36, shown in the block diagram of FIG. 2. The flow chart of FIG. 6 is a main routine, and the flow chart of FIG. 7 is an augmentation-index (AI) determining routine.

The CPU 36 carries out Step SA1 (hereinafter, "Step" is omitted, if appropriate) to drive the air pump 24 and operate the pressure control valve 18, so as to control the cuff pressure PC to the pulse-wave detecting pressure PC1 pre-set at 50 mmHg or 60 mmHg. SA1 is followed by SA2 at which the CPU 36 reads in a one-heartbeat length of the cuff-pulse-wave signal SM supplied from the pulse-wave filter circuit 28, with the cuff pressure PC being kept at the pulse-wave detecting pressure PC1.

Subsequently, the CPU 36 implements SA3 to start quickly increasing the cuff pressure PC. SA3 is followed by SA4 to judge whether the cuff pressure PC is equal to or higher than a pre-set target pressure value PC2 (i.e., 180 mmHg). The CPU repeats this step and continues quick increasing of the cuff pressure PC till a positive or affirmative judgment is made at SA4. In the meantime, if an affirmative judgment is made at SA4, the control of the CPU 36 goes to SA5 to stop the air pump 24 and operate the pressure control valve 18 so as to slowly decrease the cuff pressure PC at a rate of about 3 mmHg/sec.

Subsequently, the CPU 36 carries out SA6 through SA9 corresponding to the blood-pressure determining means 52. At SA6, the CPU 36 reads in respective one-heartbeat lengths of the cuff-pulse-wave signal SM supplied from the pulse-wave filter circuit 28 and the cuff-pressure signal SC supplied from the static-pressure filter circuit 26. SA6 is followed by SA7 to determine a systolic blood pressure value $BP_{SYS}$, a mean blood pressure value $BP_{MEAN}$, and a diastolic blood pressure value $BP_{DIA}$, according to a known oscillometric BP determining algorithm, based on the variation of respective amplitudes of successive heartbeat-synchronous pulses of the cuff pulse wave and respective values of the cuff pressure PC at the respective times of occurrence of those amplitudes. The control flow then goes to SA8 at which the CPU 36 judges whether the determination of blood pressure values BP at SA7 has been completed. SA 6 and the following steps are repeated till an affirmative judgment is made at SA8. In the meantime, if an affirmative judgment is made at SA8, the CPU 36 carries out SA9 to operate the display device 42 to display the blood pressure values $BP_{SYS}$, $BP_{MEAN}$, and $BP_{DIA}$ determined at SA7.

Subsequently, at SA10, the CPU 36 operates the pressure control valve 18 so as to release the cuff pressure PC to an atmospheric pressure. In the flow chart of FIG. 6, SA1, SA3 through SA5, and SA10 correspond to the cuff-pressure changing means 50.

The control flow then goes to SA11 corresponding to the converting means 54. At SA11, the CPU 36 determines a relationship shown in FIG. 3, based on a minimum magnitude and a maximum magnitude of the one-heartbeat length of the cuff-pulse-wave signal SM read in at SA2, and the diastolic blood pressure $BP_{DIA}$ and the systolic blood pressure $BP_{SYS}$ determined at SA7. Further, the CPU 36 converts, according to the determined relationship, a magnitude of each point of the one-heartbeat length of the cuff-pulse wave signal SM (cuff pulse wave) read in at SA2, into a pressure value.

The CPU 36 then implements SA12 and SA13 which correspond to the correction-relationship selecting means 56. At SA 12, the CPU 36 calculates a pulse pressure PP by subtracting the diastolic blood pressure value $BP_{DIA}$ from the systolic blood pressure value $BP_{SYS}$, which blood pressure values $BP_{DIA}$ and $BP_{SYS}$ have been determined at SA7. Subsequently, at SA13, the CPU 36 selects, from the four first correction relationships shown in FIG. 4A and the four second correction relationships shown in FIG. 4B, one first correction relationship and one second correction relationship which correspond to the pulse pressure PP determined at SA12.

Subsequently, at SA14 corresponding to the pseudo-pressure-pulse-wave determining means 58, the CPU 36 calculates a proportion R of a difference of the pressure value of each point of the pulse of the cuff pulse wave from the pressure value of the minimum point of the pulse, to the pulse pressure PP. Further, the CPU 36 determines a pseudo pressure pulse wave by correcting the pressure value of each point of the pulse of the cuff pulse wave, based on the calculated proportion R, according to the first and second correction relationships selected at SA13. The determined pseudo pressure pulse wave is displayed by the display device 42.

Figure 8:
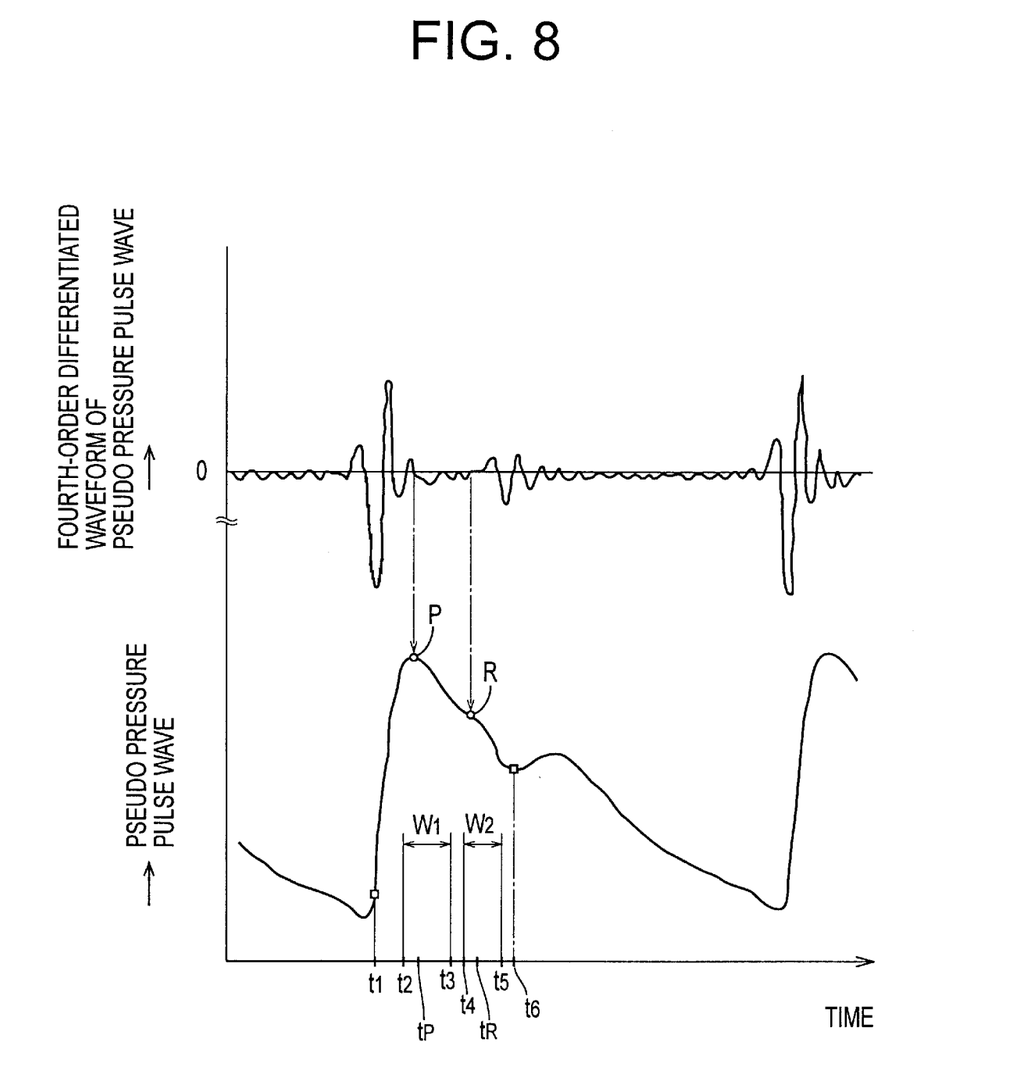
FIG. 8 is a time chart showing various points and time periods determined in the AI determining routine of FIG. 7.

The present BP measuring apparatus 10 determines the pseudo pressure pulse wave as described above. The determined pseudo pressure pulse wave displayed by the display device 42 is advantageously utilized for making a diagnosis on the patient. In the present BP measuring apparatus 10, further, an augmentation index AI is determined by implementing the augmentation-index (AI) determining routine of FIG. 7. FIG. 8 shows a time chart indicating various points and time periods determined in the augmentation-index determining routine of FIG. 7.

First, at SB1 of the control routine of FIG. 7, the CPU 36 determines, based on the waveform of the pulse of the pseudo pressure pulse wave determined at SA14 of the control routine of FIG. 6, a rising point $t_1$ and a notch point $t_6$. For instance, the CPU 36 determines, as the rising point $t_1$, a point that is subsequent to the minimum point of the pulse of the pseudo pressure pulse wave and has a magnitude equal to a prescribed proportion, e.g., one tenth, of an amplitude between the minimum point and a maximum point of the pulse, and additionally determines, as the notch point $t_6$, the first local minimum point, or the first inflection point, subsequent to the maximum point.

Subsequently, at SB2, the CPU 36 determines a rising-point window (i.e., a time gate) $W_1$ that starts and ends at a time $t_2$ and a time $t_3$, respectively, that are subsequent by respective prescribed times to the rising point $t_1$, and additionally determines a notch-point window (a time gate) $W_2$ that starts and ends at a time $t_4$ and a time $t_5$, respectively, that are prior by respective prescribed times to the notch point $t_6$.

The control then goes to SB3 at which the CPU 36 subjects, to fourth-order differentiation, the pseudo pressure pulse wave determined at SA14 of the flow chart of FIG. 6. SB3 is followed by SB4 at which the CPU 36 determines, based on two zero-crossing points of the thus obtained fourth-order differentiated waveform that fall within the rising-point window $W_1$ and the notch-point window $W_2$, respectively, a peak point P of an incident-wave component of the pseudo pressure pulse wave, a time $t_P$ of occurrence of the peak point P, a peak point R of a reflected-wave component of the pseudo pressure pulse wave, and a time $t_R$ of occurrence of the peak point R.

Subsequently, at SB5, the CPU 36 first determines a difference ΔP of the pressure of the pseudo pressure pulse wave at the time $t_P$ of occurrence of peak point of the incident-wave component from the pressure of the pseudo pressure pulse wave at the time $t_R$ of occurrence of peak point of the reflected-wave component. Further, the CPU 36 determines an augmentation index AI, by substituting the determined difference ΔP and the pulse pressure PP determined at SA12 of the flow chart of FIG. 6, with Expression (2). SB 5 is followed by SB6 at which the CPU 36 operates the display device 42 to display the augmentation index AI determined at SB5. SA12 of the flow chart of FIG. 6 and SB1 through SB 6 of the flow chart of FIG. 7 correspond to the augmentation-index determining means 60.

In the BP measuring apparatus 10 constructed as described above, a magnitude of each point of the pulse of the cuff pulse wave extracted by the pulse-wave filter circuit 28 is converted into a pressure value by the converting means 54 (SA11), based on the blood pressure values BP determined by the BP determining means 52 (SA6 through SA9). Further, the pseudo-pressure-pulse-wave determining means 58 (SA12 and SA13) determines a pseudo pressure pulse wave by correcting the respective pressure values of the respective points of the pulse, provided by the converting means 54. According to this arrangement, a medical person can make a diagnosis on the patient based on the determined pseudo pressure pulse wave while utilizing the common knowledge on pressure pulse wave, without a need of detecting an actual pressure pulse wave by using an expensive pressure pulse wave detecting apparatus that requires a cumbersome or difficult operation in detecting the pressure pulse wave.

In the present BP measuring apparatus 10, the pseudo-pressure-pulse-wave determining means 58 employs the first correction relationship for correcting the pressure values of the respective points of the first portion of the pulse of the cuff pulse wave that precedes the maximum point of the pulse, and the second correction relationship for correcting the pressure values of the respective points of the second portion of the pulse of the cuff pulse wave that follows the maximum point of the pulse, the first correction relationship and the second correction relationship differing from each other. This arrangement assures that the determined pseudo pressure pulse wave is more similar to a true pressure pulse wave. Accordingly, a more accurate diagnosis using the pseudo pressure pulse wave can be carried out.

In the present BP measuring apparatus 10, the pseudo-pressure-pulse-wave determining means 58 selects, from a plurality of correction relationships corresponding to a plurality of pulse-pressure ranges, a correction relationship based on the pulse pressure PP obtained from the blood pressure values BP determined by the BP determining means 52. Further, the pseudo-pressure-pulse-wave determining means 58 determines the pseudo pressure pulse wave, according to the selected correction relationship. According to this arrangement, the correction relationship used where the pulse pressure PP is small differs from that used where the pulse pressure PP is great. Therefore, the determined pseudo pressure pulse wave is more similar to a true pressure pulse wave.

While the present invention has been described in detail in its presently preferred embodiment, by reference to the drawings, the invention may otherwise be embodied.

In the illustrated BP measuring apparatus 10, the cuff pressure PC is kept at the pulse-wave detecting pressure PC1 prior to the blood pressure measurement, and the pseudo pressure pulse wave is determined based on the cuff pulse wave detected when the cuff pressure PC is kept at the pulse-wave detecting pressure PC1. The cuff pressure PC may be controlled to the pulse-wave detecting pressure after the blood pressure measurement, and the cuff pulse wave used for determining the pseudo pressure pulse wave may be detected after the blood pressure measurement. Further, the cuff pulse wave used for determining the pseudo pressure pulse wave may be detected while the cuff pressure PC is changed for the blood pressure measurement. Where the cuff pulse wave is detected after the blood pressure measurement, it is preferable to detect the cuff pulse wave after the tissue of the subject which has been deformed due to the pressing by the cuff during the blood pressure measurement returns to its normal state prior to the pressing by the cuff. For instance, it is preferable to detect a cuff pulse wave several tens of seconds after the blood pressure measurement.

In the BP measuring apparatus 10 constructed as described above, the common correction relationship is used for different subjects. Respective different correction relationships may be determined for respective different subjects.

In the BP measuring apparatus 10 constructed as described above, the respective different four correction relationships are used for the respective different four pulse-pressure ranges. Only one correction relationship may be used irrespective of the magnitude of the pulse pressure PP. Alternatively, five or more correction relationships may be used.

In the illustrated BP measuring apparatus 10, the pressure values of the respective points of the first portion of the pulse of the cuff pulse wave that precedes the maximum point of the pulse are corrected according to the first correction relationship, and the pressure values of the respective points of the second portion of the pulse of the cuff pulse wave that follows the maximum point of the pulse are corrected according to the second correction relationship that differs from the first correction relationship. A common correction relationship may be used for correcting the pressure values of the points of the first portion of the pulse and the pressure values of the points of the second portion of the pulse.

Each correction relationship used in the illustrated BP measuring apparatus 10 is determined such that the correction amount linearly changes with the change of the proportion R of the difference of the pressure value of each point of the pulse of the cuff pulse wave from the minimum point of the pulse, to the pulse pressure PP. The correction relationship may be determined such that the correction amount changes in steps.

In the illustrated BP measuring apparatus 10, the cuff 12 is worn on the upper arm 14 of the subject. The cuff 12 may be worn on a femoral portion or an ankle of the subject.

In the illustrated BP measuring apparatus 10, the blood pressure values are determined according to the oscillometric method. The blood pressure values may be determined according to a so-called "K-sound" method in which the blood pressure values are determined based on cuff pressures at times of occurrence and extinction of Korotkoff sounds. Alternatively, the blood pressure values may be determined according to an ultrasonic Doppler method in which opening and closing of an arterial duct are detected, during changing of cuff pressure, by ultrasonic oscillator and receiver that are disposed right above the artery.

In the illustrated BP measuring apparatus 10, the determined pseudo pressure pulse wave is displayed by the display device 42, and in addition, the augmentation index AI is determined based on the pseudo pressure pulse wave. The BP measuring apparatus 10 may be arranged to carry out either one of displaying the pseudo pressure pulse wave and determining the augmentation index AI. Further, the BP measuring apparatus 10 may be arranged such that, in place of, or in addition to, the augmentation index AI, any other physical information of the subject is obtained from the pseudo pressure pulse wave. For instance, the BP measuring apparatus 10 may be arranged to obtain physical information "%MAP" that is a proportion (=100×G/H (%)) of a height, G, of a gravity center of an area of a pulse, to a height H of the peak of the pulse, i.e., pulse pressure PP.

It is to be understood that the present invention may be embodied with other changes, improvements and modifications that may occur to one skilled in the art without departing from the spirit and scope of the invention.

What is claimed is:

1. A blood pressure measuring apparatus, comprising a cuff which is adapted to be worn on a body portion of a living subject, said blood pressure measuring apparatus determining a blood pressure value of the subject based on a signal which is obtained from the cuff when a pressure in the cuff is changed, wherein the improvements comprise:

a cuff pulse wave detecting device which detects a cuff pulse wave as a pulse wave which is produced from an artery of the subject and is transmitted to the cuff, the cuff pulse wave comprising at least one heartbeat-synchronous pulse which is produced from the artery in synchronism with at least one heartbeat of the subject;

a converting means for converting, based on the blood pressure value determined by the apparatus, a magnitude of each point of the heartbeat-synchronous pulse of the cuff pulse wave, into a pressure value; and a pseudo-pressure-pulse-wave determining means for determining a pseudo pressure pulse wave by correcting the respective pressure values of the respective points of the heartbeat-synchronous pulse, provided by the converting means, according to at least one correction relationship between (A) a proportion of the difference of pressure values of each point of heartbeat-synchronous pulse from a pressure value of minimum point of the pulse, to pulse pressure which is the difference of the pressure value of maximum point of the pulse from the pressure value of the minimum point of the pulse, and (B) correction amount, in which greater correction amount corresponds to greater proportion.

2. A blood pressure measuring apparatus according to claim 1, wherein the pseudo-pressure-pulse-wave determining means determines a first portion of the pseudo pressure pulse wave by correcting the respective pressure values of the respective points of a first portion of the heartbeat-synchronous pulse that precedes the maximum point of the pulse, according to a first correction relationship, and determines a second portion of the pseudo pressure pulse wave by correcting the respective pressure values of the respective points of a second portion of the pulse that follows the maximum point of the pulse, according to a second correction relationship differing from the first correction relationship.

3. A blood pressure measuring apparatus according to claim 1, wherein the pseudo-pressure-pulse-wave determining means selects, from a plurality of correction relationships corresponding to a plurality of pulse-pressure ranges, one correction relationship based on a pulse pressure determined based on blood pressure values determined by the apparatus, and determines the pseudo pressure pulse wave by correcting the respective pressure values of the respective points of the heartbeat-synchronous pulse, according to said one correction relationship.

4. A blood pressure measuring apparatus according to claim 1, wherein the pseudo-pressure-pulse-wave determining means corrects the pressure values of the points of the heartbeat-synchronous pulse of the cuff pulse wave, by subtracting, from the pressure values of the points, correction amounts determined for the respective points according to the correction relationship.

5. A blood pressure measuring apparatus according to claim 1, wherein the converting means converts, into the pressure values, the magnitudes of the points of the heartbeat-synchronous pulse, based on a relationship between magnitude of each point of heartbeat-synchronous pulse and blood pressure.

6. A blood pressure measuring apparatus according to claim 1, further comprising:

a cuff-pressure changing means for changing the pressure in the cuff;

a display device by which the pseudo pressure pulse wave determined by the pseudo-pressure-pulse-wave determining means is displayed; and an augmentation-index determining means for determining an augmentation index, based on the pseudo pressure pulse wave determined by the pseudo-pressure-pulse-wave determining means, the augmentation index being a proportion of a difference of a pressure of the pseudo pressure pulse wave at a time of occurrence of a peak point of an incident wave component thereof, from a pressure of the pseudo pressure pulse wave at a time of occurrence of a peak point of a reflected wave component thereof, to a pulse pressure of the pseudo pressure pulse wave.

7. A blood pressure measuring apparatus, comprising a cuff which is adapted to be worn on a body portion of a living subject, said blood pressure measuring apparatus determining a blood pressure value of the subject based on a signal which is obtained from the cuff when a pressure in the cuff is changed, wherein the improvements comprise:

a cuff pulse wave detecting device which detects a cuff pulse wave as a pulse wave which is produced from an artery of the subject and is transmitted to the cuff, the cuff pulse wave comprising at least one heartbeat-synchronous pulse which is produced from the artery in synchronism with at least one heartbeat of the subject;

a converting device which converts, based on the blood pressure value determined by the apparatus, a magnitude of each point of the heartbeat-synchronous pulse of the cuff pulse wave, into a pressure value; and a pseudo-pressure-pulse-wave determining device which determines a pseudo pressure pulse wave by correcting the respective pressure values of the respective points of the heartbeat-synchronous pulse, provided by the converting device, according to at least one correction relationship between (A) proportion of difference of pressure value: of each point of heartbeat-synchronous pulse from pressure value of minimum point of the pulse, to pulse pressure as difference of pressure value of maximum point of the pulse from the pressure value of the minimum point of the pulse, and (B) correction amount, in which greater correction amount corresponds to greater proportion.

* * * * *